United States Patent [19]
Phelan

[11] Patent Number: 5,500,973
[45] Date of Patent: Mar. 26, 1996

[54] HYDRO POWERED PLAQUE REMOVER

[76] Inventor: John J. Phelan, 109 Jeanette Ave., Inwood, N.Y. 11696

[21] Appl. No.: 438,102

[22] Filed: May 8, 1995

[51] Int. Cl.$^6$ .......................... A61C 17/30; A46B 11/06
[52] U.S. Cl. .................. 15/29; 401/287; 401/289
[58] Field of Search ............. 15/24, 29; 401/270, 401/278, 279, 282, 286, 287–290

[56] References Cited

U.S. PATENT DOCUMENTS

| | | | |
|---|---|---|---|
| 2,855,619 | 10/1958 | Graham | 401/289 |
| 3,039,123 | 6/1962 | Brucker et al. | 15/29 |
| 3,135,989 | 6/1964 | Gatti | 401/289 |

*Primary Examiner*—Edward L. Roberts, Jr.
*Attorney, Agent, or Firm*—Richard L. Miller

[57] ABSTRACT

A plaque removing device adaptable to a water supply and which includes a flexible conduit, an interchangeable toothbrush, a plurality of bristles, and a rinse reservoir. The flexible conduit contains a rinse conduit and at least one water conduit. The flexible conduit has a flexible conduit first end that is connectable to the water supply and a flexible conduit second end. The interchangeable toothbrush has an interchangeable toothbrush head portion and contains a rinse passageway that communicates with the water conduit and at least one water passageway that communicates with the at least one water conduit. The toothbrush is disconnectingly attached to the flexible conduit second end so that the interchangeable toothbrush can be changed for user preference. The plurality of bristles are located on the toothbrush head portion and communicate with both the rinse passageway and the at least one water passageway. The rinse reservoir is located in the rinse conduit and contains a rinse so that water from the water supply passes through the water conduit and the water passageway and ultimately is deposited on the plurality of bristles and the rinse passes through the rinse conduit and the rinse passageway and ultimately is deposited on the plurality of bristles.

11 Claims, 1 Drawing Sheet

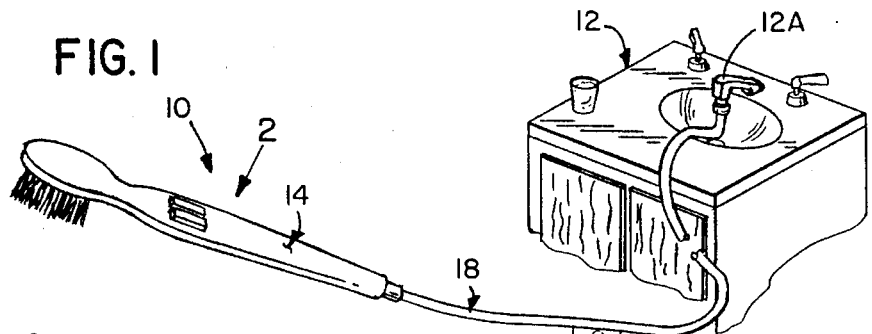
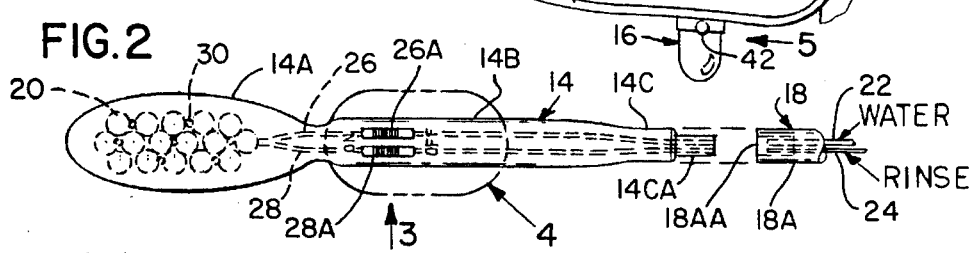
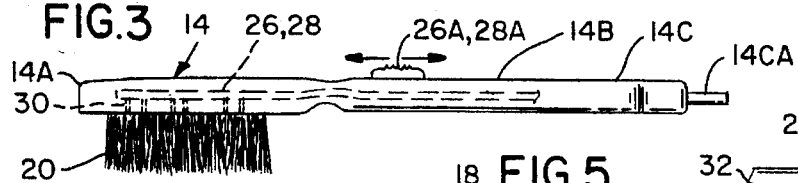
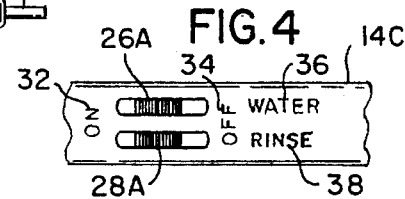
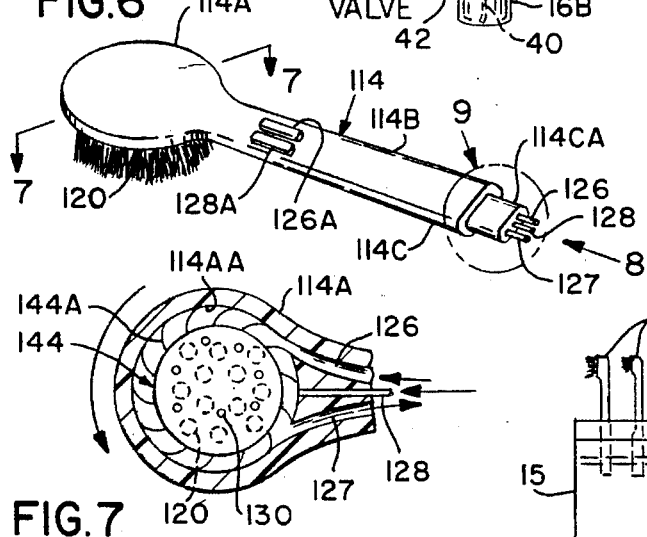
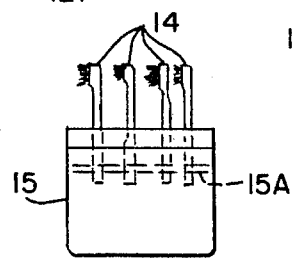
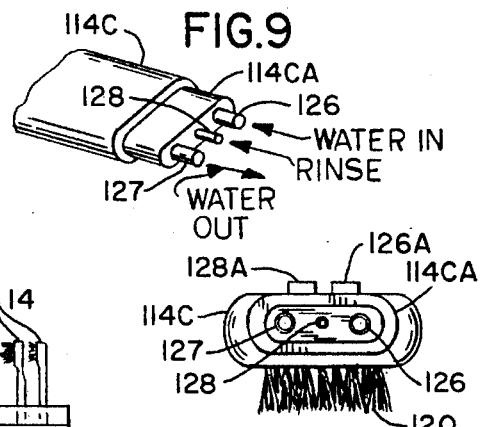

HYDRO POWERED PLAQUE REMOVER

BACKGROUND OF THE INVENTION

The present invention relates to a hydro powered plaque remover. More particularly, the present invention relates to a hydro powered plaque remover that delivers a cleaning mixture to the brush bristles.

Dental plaque is a colony of bacteria held together by viscid substances called glucans which also help anchor the bacteria to the teeth. Bacteria account for approximately 70% of the plaque mass. Glucans account for 20%, and levans, which act as energy sources, account for the remaining 10%.

When the saliva comes in contact with the bare tooth enamel, a thin amorphous film mainly of glycoproteins rapidly forms on the surface of the tooth. Glycoproteins are molecules with a protein that is combined with carbohydrates. This film is called the acquired pellicle. The acquired pellicle is less than one micron in thickness. The actual binding of the glycoproteins to the enamels cells is accomplished by means of electrostatic differences between the two. As an example, a protein with a negative charge would adhere to a site on the tooth surface that has a positive charge. At this initial stage, the acquired pellicle has no colonies of bacteria.

The dental plaque attaches itself to the acquired pellicle proteins by interactions similar to the attachment of the proteins to the bare tooth enamel, that is, by means of electrostatic differences between the pellicle and the bacterial wall and the glucans. Colonization of the pellicle by the bacteria signals the formation of dental plaque. By means of electrostatic charges the bacterial cells adhere to the pellicle, cell walls of the other bacteria or glucans making up the intercellular matrix of the plaque.

Processes for removal of dental plaque have involved the physical scraping of the teeth alone or in combination with ultrasonics and water sprays.

Numerous innovations for plaque removing devices have been provided in the prior art. Even though these innovations may be suitable for the specific individual purposes to which they address, they differ from the present invention in that none teach a water drive rotary toothbrush which includes a rinse reservoir for delivering a rinse into the brush bristles.

For example, U.S. Pat. No. 3,909,867 to Hogswell teaches a rotary toothbrush that includes a hand held housing and a toothbrush that is interchangeably mounted on a rotary shaft that is journalled in the housing. A turbine wheel is mounted in a chamber that is contained in the housing and rotates a shaft when water under pressure is supplied to the housing chamber. A manually operable control is mounted on the housing to drive the wheel in either direction or to stop it. Water injectors that are located in the housing chamber cause a pressure reduction in the chamber between the turbine wheel and a water outlet. Channels in the shaft supply rinsing water from the housing chamber to the brush.

Another example, U.S. Pat. No. 4,655,198 to Hommann teaches a hand held appliance for mouth a tooth care that includes a grip portion that has a manipulating element that acts as a sliding switch and which is capable of being shifted in an axial direction. A push button is guided on inclined surfaced in the interior of the shell of the grip portion and reaches through a slot in the shell as well as through a cutout in the manipulating element. In the interior of the grip portion, the push button rests on a pinch tube via a ball.

Still another example, U.S. Pat. No. 4,808,109 to Thornton teaches a process that involves the application of heated water, above 40 degrees C., to the teeth with simultaneous rotary brushing. The apparatus is a turbine power unit that is adapted to be connected to the heated water faucet and to sit in the sink. A heated water exhaust conduit from the unit and a flexible power shaft lead to a handpiece which has a rotary brush driven by the shaft and a nozzle that is connected to the conduit and directed at the brush.

Finally, another example, U.S. Pat. No. 5,273,428 to Fischer teaches a dental cleaning nozzle that has a brush element combined with a water jet. The jet is directed to provide interaction with the brush element with a part of the jet bypassing the end of the brush element.

As can be readily seen, numerous innovations for plaque removing devices have been provided in the prior art that are adapted to be used. However, even though these innovations may be suitable for the specific individual purposes to which they address, they are not suitable for the purposes of the present invention as heretofore described.

SUMMARY OF THE INVENTION

Accordingly, it is an object of the present invention to provide a hydro powered plaque remover that avoids the disadvantages of the prior art.

Another object of the present invention is to provide a hydro powered plaque remover that is simple and inexpensive to manufacture.

Still another object of the present invention is to provide a hydro powered plaque remover that is simple to use.

Yet another object of the present invention is to provide a hydro powered plaque remover that is adaptable to any faucet.

Still another object of the present invention is to provide a hydro powered plaque remover that can be hooked up directly to an existing plumbing system.

Yet still another object of the present invention is to provide a hydro powered plaque remover that includes a flexible conduit, an interchangeable toothbrush, a plurality of bristles, and a rinse reservoir.

Still yet another object of the present invention is to provide a hydro powered plaque remover wherein the flexible conduit contains a rinse conduit and at least on water conduit.

Yet still another object of the present invention is to provide a hydro powered plaque remover wherein the flexible conduit has a flexible conduit first end that is connectable to the water supply and a flexible conduit second end, Still yet another object of the present invention is to provide a hydro powered plaque remover wherein the interchangeable toothbrush has a interchangeable toothbrush head portion and contains a rinse passageway that communicates with the water conduit and at least one water passageway that communicates with the at least one water conduit, Yet still another object of the present invention is to provide a hydro powered plaque remover wherein the toothbrush is disconnectingly attached to the flexible conduit second end so that the interchangeable toothbrush can be changed for user preference, Still yet another object of the present invention is to provide a hydro powered plaque remover wherein the plurality of bristles are located on the toothbrush head portion and communicate with both the rinse passageway and the at least one water passageway, Yet still another object of the present invention is to provide a hydro powered plaque remover wherein the rinse reservoir is located in the rinse conduit and contains a rinse so that water from the water supply passes through the water conduit and the water passageway and ultimately is deposited on the plurality of bristles and the rinse passes through the rinse conduit and the rinse passageway and ultimately is deposited on the plurality of bristles.

Still yet another object of the present invention is to provide a hydro powered plaque remover that further includes a water passageway switch that is located in the water passageway and which regulates the amount of water entering the plurality of bristles.

Yet still another object of the present invention is to provide a hydro powered plaque remover that further includes a rinse passageway switch that is located in the rinse passageway and which regulates the amount of rinse entering the plurality of bristles.

Still yet another object of the present invention is to provide a hydro powered plaque remover wherein the water passageway switch is hand operable.

Yet still another object of the present invention is to provide a hydro powered plaque remover wherein the rinse passageway switch is hand operable.

Still yet another object of the present invention is to provide a hydro powered plaque remover wherein the rinse is selected from a group that includes concentrated mouthwash, fluoride rinse, hydrogen peroxide, and baking soda solution.

Yet still another object of the present invention is to provide a hydro powered plaque remover that further includes a turbine contained within the interchangeable toothbrush head portion and which is connected to the plurality of bristles.

Still yet another object of the present invention is to provide a hydro powered plaque remover wherein the at least one water passageway is two.

Yet still another object of the present invention is to provide a hydro powered plaque remover wherein one of the two water passageways carries water to the turbine and the other of the two passageways carries water away from the turbine so that water entering and leaving the turbine causes the turbine to revolve.

Still yet another object of the present invention is to provide a hydro powered plaque remover that further includes a stand for holding each interchangeable toothbrush.

Finally, another object of the present invention is to provide a hydro powered plaque remover wherein the rinse reservoir has a rinse shut off valve.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

FIG. 1 is a diagrammatic perspective view of the instant invention attached to a typical sink faucet;

FIG. 2 is an enlarged top plan view taken in the direction of arrow 2 of FIG. 1;

FIG. 2A is a diagrammatic view illustrating a typical set of brush heads of the instant invention so that each of a family can have his own;

FIG. 3 is a side elevational view taken in the direction of arrow 3 in FIG. 3;

FIG. 4 is an enlarged partial view taken in the area enclosed by the dotted oval indicated by arrow 4 in FIG. 2 illustrating typical valve controls for water and rinse;

FIG. 5 is a diagrammatic view taken in the direction of arrow 5 in FIG. 1 illustrating a typical rinse container with shut off valve;

FIG. 6 is a diagrammatic perspective view of a second embodiment of the instant invention;

FIG. 7 is an enlarged diagrammatic cross sectional view with parts broken away taken on line 7—7 of FIG. 6;

FIG. 8 is an enlarged end view taken in the direction of arrow 8 in FIG. 6; and

FIG. 9 is an enlarged diagrammatic prospective view taken in the area enclosed by the dotted circle indicated by arrow 9 in FIG. 6.

DETAILED DESCRIPTION OF THE PREFERRED EMBODIMENT

Referring now to the figures in which like numerals indicate like parts, and with particularity to FIG. 1, the hydro powered plaque remover of the present invention is shown generally at 10 connected to a sink faucet 12A of a sink 12. It is to be noted that the hydro powered plaque remover 10 can also be connected directly to a plumbing system water supply.

The hydro powered plaque remover 10 includes an interchangeable toothbrush 14, a rinse reservoir 16, and a flexible conduit 18 which fluidly connects the interchangeable toothbrush 14 to the sink faucet 12A. The flexible conduit 18 disconnectingly receives the interchangeable toothbrush 14, carries water from the sink faucet 12A, and carries a rinse from the rinse reservoir 16 to the interchangeable toothbrush 14. Since the interchangeable toothbrush 14 is disconnectingly received by the flexible conduit 18, each user can use a different interchangeable toothbrush 14, if so desired. As shown in FIG. 2A, the interchangeable toothbrush 14 can be stored in a rack 15 by insertion into a cross member 15A.

As can be seen in FIGS. 2 and 3, the interchangeable toothbrush 14 has a toothbrush head portion 14A, a toothbrush intermediate portion 14B, and a toothbrush tail portion 14C with a toothbrush tail portion projection 14CA. A plurality of bristles 20 are disposed on the toothbrush head portion 14A.

The flexible conduit 18 has a flexible conduit end 18A that contains a flexible conduit end chamber 18AA. The interchangeable feature of the interchangeable toothbrush 14 is accomplished by the toothbrush tail portion projection 14CB being removably received by the flexible conduit end chamber 18AA. This allows the interchangeable toothbrush 14 to be disconnected from the flexible conduit 18.

The flexible conduit 18 contains a water conduit 22 and a rinse conduit 24. The water conduit 22 carries water from the sink faucet 12A to the interchangeable toothbrush 14 while a water passageway 26 contained in the interchangeable toothbrush 14 carries the water to the toothbrush head portion 14A. The rinse conduit 24 carries rinse from the rinse reservoir 16 to the interchangeable toothbrush 14 while a rinse passageway 28 contained in the interchangeable toothbrush 14 carries the rinse to the toothbrush head portion 14A. The water conduit 26 and the rinse conduit 28 merge at the toothbrush head portion 14A and the water and the rinse are both feed to the plurality of bristles 20 through mixer passageways 30 contained in the toothbrush head 14A.

The rinse may be a concentrated mouthwash, fluoride rinse, hydrogen peroxide, baking soda and water, or any combination thereof.

A water passageway switch 26A and a rinse passageway switch 28A are located in the interchangeable toothbrush intermediate portion 14 and are movable through an on and off position. The water passageway switch 26A provides control of the amount of water delivered to the plurality of bristles while the rinse passageway switch 28A provides control of the amount of rinse delivered to the plurality of bristles 20. The use of both the water passageway switch 26A and the rinse passageway switch 28A allow the amount of the water and the rinse delivered to the plurality of bristles 20 to be regulated by user preference. The amount of delivery being from completely on to completely off or any amount therebetween.

By referring to FIG. 4, the descriptive indicia regarding the use of the water passageway switch 26A and the rinse passageway switch 28A, can best be seen. "ON" indicia 32 indicates the on position while "OFF" indicia 34 indicates the off position. Further shown is "WATER" indicia 36 indicating the water passageway switch 26A and "RINSE" indicia 38 indicating the rinse passageway switch 28A.

The configuration of the rinse reservoir 16 can best be seen in FIG. 5, and as such, will be discussed with reference thereto. The rinse reservoir 16 has a rinse reservoir cap 16A and a rinse reservoir container 16B. The flexible conduit 18 is attached to the rinse reservoir cap 16A and fluidly communicates with the rinse reservoir container 16B by a pick up tube 40. A rinse shut off valve 42, located on the rinse reservoir cap 16A, communicates with the pick up tube 40.

In operation, the free end of the flexible conduit 18 is connected to the sink faucet 12A or to a plumbing system water supply. The rinse reservoir container 16B is removed, filled with rinse, and replaced. If it is desired to use rinse, the rinse shut off switch is opened. A respective interchangeable toothbrush 14 is removed from the rack 15 and attached to the flexible conduit 18 and gripped in the hand of the user while the user's thump rests over the water passageway switch 26A and the rinse passageway switch 28A. Based on the amount of water and/or rinse desired by the user, the user uses his thumb to move the water passageway switch 26A and the rinse passageway switch 28A to the desired position.

Referring now to FIGS. 7 through 9, an alternate embodiment of the interchangeable toothbrush is shown generally at 110 and includes a toothbrush head portion 114A, a toothbrush intermediate portion 114B, and a toothbrush tail portion 114C with a toothbrush tail portion projection 114CA. A plurality of bristles 120 are rotatively mounted on the toothbrush head portion 114A. The interchangeable toothbrush head portion 114A contains an interchangeable head portion chamber 114AA in which is located a turbine 144. The plurality of bristles 120 are connected to the turbine 144 and revolve therewith in the same direction. The plane of the plurality of bristles 120 is substantially parallel to that of the turbine 144. The perimeter of the turbine 144 is covered with a plurality of turbine fins 144A.

A water input passageway 126 is contained in the interchangeable toothbrush 114 and carries water to the toothbrush head portion chamber 114A. A water output passageway 127 is contained in the interchangeable toothbrush 114 and carries water away from the toothbrush head portion chamber 114A. A rinse passageway 128 contained in the interchangeable toothbrush 114 carries the rinse to the toothbrush head portion 114A. The water and the rinse are both fed to the plurality of bristles 120 through mixer passageways 130 contained in the toothbrush head 114A. When water enters the interchangeable toothbrush head portion chamber 114AA it contacts and pushes the turbine fins 144A which causes the turbine 144 to revolve. Since the plurality of bristles 120 are mounted to the turbine 144 they to revolve imparting rotary action to the tooth cleaning.

A water passageway switch 126A and a rinse passageway switch 128A are located in the interchangeable toothbrush intermediate portion 114 and are movable through an on and off position. The water passageway switch 126A provides control of the amount of water delivered to the plurality of bristles 120 while the rinse passageway switch 128A provides control of the amount of rinse delivered to the plurality of bristles 120. The use of both the water passageway switch 126A and the rinse passageway switch 128A allow the amount of the water and the rinse delivered to the plurality of bristles 120 to be regulated by user preference. The amount of delivery being from completely on to completely off or any amount therebetween.

It will be understood that each of the elements described above, or two or more together, may also find a useful application in other types of constructions differing from the type described above.

While the invention has been illustrated and described as embodied in a hydro powered plaque remover, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

The invention claimed is:

1. A plaque removing device adaptable to a water supply, comprising:

a) a flexible conduit containing a rinse conduit and at least one water conduit, said flexible conduit having a flexible conduit first end connectable to said water supply and a flexible conduit second end;

b) an interchangeable toothbrush having a interchangeable toothbrush head portion and containing a rinse passageway communicating with said rinse conduit and at least one water passageway communicating with said at least one water conduit, said toothbrush being disconnectingly attached to said flexible conduit second end so that said interchangeable toothbrush can be changed for user preference;

c) a plurality of bristles disposed on said toothbrush head portion and communicating with both said rinse passageway and said at least one water passageway;

e) a rinse reservoir disposed in said rinse conduit and containing a rinse so that water from said water supply passes through said water conduit and said water passageway and ultimately is deposited on said plurality of bristles and said rinse passes through said rinse conduit and said rinse passageway and ultimately is deposited on said plurality of bristles.

2. The device as defined in claim 1, further comprising a water passageway switch disposed in said water passageway and regulating the amount of water entering said plurality of bristles.

3. The device as defined in claim 2, wherein said water passageway switch is hand operable.

4. The device as defined in claim 1, further comprising a rinse passageway switch disposed in said rinse passageway and regulating the amount of rinse entering said plurality of bristles.

5. The device as defined in claim 3, wherein said rinse passageway switch is hand operable.

6. The device as defined in claim 1, wherein said rinse is selected from a group consisting of concentrated mouthwash, fluoride rinse, hydrogen peroxide and baking soda solution.

7. The device as defined in claim 1, further comprising a turbine contained within said interchangeable toothbrush head portion and connected to said plurality of bristles.

8. The device as defined in claim 7, wherein said at least one water passageway is two.

9. The device as defined in claim 8, wherein one of said two water passageways carries water to said turbine and other of said two passageways carries water away from said turbine so that water entering and leaving said turbine causes said turbine to revolve.

10. The device as defined in claim 1, further comprising a stand for holding each said interchangeable toothbrush.

11. The device as defined in claim 1, wherein said rinse reservoir has a rinse shut off valve.

* * * * *